(12) United States Patent
Tzvetkov

(10) Patent No.: US 9,738,640 B2
(45) Date of Patent: Aug. 22, 2017

(54) SUBSTITUTED BENZAMIDE DERIVATIVES AS IN VITRO MAO-B INHIBITORS

(71) Applicant: "NTZ LAB" Ltd., Sofia (BG)

(72) Inventor: Nikolay Tzvetkov, Sofia (BG)

(73) Assignee: "NTZ LAB" LTD., Sofia (BG)

( * ) Notice: Subject to any disclaimer, the term of this patent is extended or adjusted under 35 U.S.C. 154(b) by 0 days.

(21) Appl. No.: 14/904,893

(22) PCT Filed: Jul. 11, 2014

(86) PCT No.: PCT/BG2014/000027
§ 371 (c)(1),
(2) Date: Jan. 13, 2016

(87) PCT Pub. No.: WO2015/013777
PCT Pub. Date: Feb. 5, 2015

(65) Prior Publication Data
US 2016/0152611 A1    Jun. 2, 2016

(30) Foreign Application Priority Data

Jul. 29, 2013   (BG) ........................................ 111544

(51) Int. Cl.
*C07D 471/04* (2006.01)
*A61K 31/437* (2006.01)

(52) U.S. Cl.
CPC .......... *C07D 471/04* (2013.01); *A61K 31/437* (2013.01)

(58) Field of Classification Search
None
See application file for complete search history.

(56) References Cited

U.S. PATENT DOCUMENTS

2010/0069430 A1   3/2010   Kim et al.

FOREIGN PATENT DOCUMENTS

| EP | 0 842 934 A1 | 5/1998 |
|---|---|---|
| WO | 2005/004801 A2 | 1/2005 |
| WO | 2009/061730 A2 | 5/2009 |

OTHER PUBLICATIONS

STN Chemical Database Registry for RN 1387436-08-9, CN Benzamide, 3,4-dichloro-N-1H-indol-5-yl—(CA Index Name), ED Entered STN: Aug. 7, 2012.*
Online "http://web.archive.org/web/20090428093726/http://www.ukrorgsynth.com/bb.php" dated to Apr. 28, 2009 accessed Nov. 22, 2016.*

(Continued)

*Primary Examiner* — David K O'Dell
(74) *Attorney, Agent, or Firm* — Baker & Hostetler LLP

(57) ABSTRACT

The invention relates to the use of substituted benzamide derivatives of Formula I: Wherein: $A^1$ and $A^2$ are —N or —CH, so that if $A^1$ is —N, then $A^2$ is —CH and If $A^2$ is —N, then $A^1$ is —CH; R is a hydrogen atom, or represents branched or unbranched —$(C_1$-$C_3)$-alkyl, —$(C_1$-$C_3)$-alkyl, wherein one, two or three hydrogen atoms may be substituted by a halogen or hydroxyl, —$(C_1$-$C_3)$—O—$(C_1$-$C_3)$, —$(C_1$-$C_3)$—O—$(C_1$-$C_3)$, wherein one, two or three hydrogen atoms may be substituted by a halogen, or R is a group wherein $R^3$ and $R^4$ both together or independently are halogen, hydroxyl, —$(C_1$-$C_3)$alkyl, wherein one, two or three hydrogen atoms may be substituted by a halogen or hydroxyl, —O—$(C_1$-$C_3)$-alkyl, —O—$(C_1$-$C_3)$-alkyl, wherein one, two or three hydrogen atoms may be substituted by a halogen, —O—$(C_1$-$C_3)$—O—$(C_1$-$C_3)$, —O—$(C_1$-$C_3)$—O—$(C_1$-$C_3)$, wherein one, two or three hydrogen atoms may be substituted by a halogen; $R^1$ and $R^2$ both together or independently are halogen, hydroxyl, —$(C_1$-$C_3)$-alkyl, —$(C_1$-$C_3C)$-alkyl, wherein one, two or three hydrogen atoms may be substituted by a halogen or hydroxyl, —O—$(C_1$-$C_3)$-alkyl, —O—$(C_1$-$C_3)$-alkyl, wherein one, two or three hydrogen atoms may be substituted by a halogen, —O—$(C_1$-$C_3)$—O—$(C_1$-$C_3)$, -0-$(C_1C_3)$—O—$(C_1C_3)$, wherein one, two or three hydrogen atoms may be substituted by a halogen, their pharmaceutically acceptable salts, isomers or mixtures thereof as in vitro selective MAO-B inhibitors. The substituted benzamide derivatives of Formula I, their pharmaceutically acceptable salts, isomers or mixtures thereof are useful for the manufacture of a medicament for prevention and treatment of acute and chronic neurological disorders, cognitive and neurodegenerative diseases, more precisely for the manufacture of a medicament for prevention and treatment of neurodegenerative disorders such as Parkinson's Disease and Alzheimer's Disease.

2 Claims, 1 Drawing Sheet

(56) References Cited

OTHER PUBLICATIONS

Online: "http://web.archive.org/web/20090405123528/http://www.ukrorgsynth.com/screening.php" dated to Apr. 5, 2009 accessed Nov. 22, 2016.*

C. J. Fowler et al., "The Effect of Age on the Activity and Molecular Properties of Human Brain Monoamine Oxidase," J. Neural Transmission 49, 1-20 (1980).

A. Nicotra et al., "Monoamine Oxidase Expression During Development and Aging," NeuroToxicology 25 (2004), pp. 155-165.

T. Nagatsu et al., "Progress in Monoamine Oxidase (MAO) Research in Relation to Genetic Engineering," NeuroToxicology 25 (2004) pp. 11-20.

V. Perez et al., "Relevance of benzyloxy group in 2-indolyl methylamines in the selective MAO-B inhibition," British Journal of Pharmacology 127 (1999), pp. 869-876.

M. B. H. Youdim et al., "The therapeutic potential of monoamine oxidase inhibitors," Nature Reviews, Neuroscience, vol. 7, Apr. 2006, pp. 295-309.

M. Bortolato et al., "Monoamine oxidase inactivation: From pathophysiology to therapeutics," Advanced Drug Delivery Reviews 60 (2008), pp. 1527-1533.

M. S. Benedetti et al., "Monoamine Oxidase, Brain Ageing and Degenerative Diseases," Biochemical Pharmacology, vol. 38, No. 4, (1989) pp. 555-561.

L. Emilsson et al., "Increased monoamine oxidase messenger RNA expression levels in frontal cortex of Alzheimer's disease patients," Neuroscience Letters 326 (2002), pp. 56-60.

S. Filla et al., "Novel Potent 5-HT1F Receptor Agonists: Structure-Activity Studies of a Series of Substituted N-[3-(1-Methyl-4-piperidinyl)-1H-pyrrolo[3,2-b]pyridin-5-yl]amides," J. Med. Chem. 46 (2003), pp. 3060-3071.

S. Ghosh et al., "Benzoylation of Amines sans Alkali: A Green Protocol in Neat Phase," Organic Chemistry International, vol. 2010, Article ID 743186, pp. 1-3.

S. Jegham et al., "Monoamine oxidase A and B inhibitors," Expert Opinion on Therapeutic Patents (1998) vol. 8, No. 9, pp. 1143-1150.

W. M. Keung et al., "Monoamine oxidase inhibitors," Expert Opinion on Therapeutic Patents (2002) vol. 12, No. 12, pp. 1813-1829.

A. Bolasco et al., "Recent development of monoamine oxidase inhibitors," Expert Opinion on Therapeutic Patents (2005) vol. 15, No. 12, pp. 1763-1782.

A. Bolasco et al., "Focusing on new monoamine oxidase inhibitors," Expert Opinion on Therapeutic Patents (2010) vol. 20, No. 7, pp. 909-939.

S. Carradori et al., "Novel monoamine oxidase inhibitors: a patent review (2012-2014)," Expert Opinion on Therapeutic Patents (2015) vol. 25, No. 1, pp. 91-110.

Alfred W. J. Bach et al., "cDNA cloning of human liver monoamine oxidase A and B: Molecular basis of differences in enzymatic properties," Proc. Natl. Acad. Sci. USA, vol. 85, pp. 4934-4938, Jul. 1988.

Andrea M. Cesura et al., "The new generation of monoamine oxidase inhibitors," Progress in Drug Research 38, 1992, pp. 171-297.

Andrew Holt et al., "A Continuous Spectrophotometric Assay for Monoamine Oxidase and Related Enzymes in Tissue Homogenates," Analytical Biochemistry 244, Article No. AB969911, pp. 384-392, 1997.

Shaheen E. Lakhan, "From a Parkinson's disease expert: Rasagiline and the Future of Therapy," Molecular Neurodegeneration, 2(13), 2007.

Palhagen et al., "Selegiline slows the progression of the symptoms of Parkinson disease," Neurology 2006, 66(8), pp. 1200-1206.

Jacobus P. Petzer et al., "Inhibition of Monoamine Oxidase B by Selective Adenosine A2A Receptor Antagonists," Bioorganic & Medicinal Chemistry 11, 2003, pp. 1299-1310.

P. Riederer et al., "Selegiline's neuroprotective capacity revisited," Journal of Neural Transmission, 2003, 110(11), pp. 1273-1278.

Moussa B. H. Youdim et al., "New Directions in Monoamine Oxidase A and B Selective Inhibitors and Substrates," Biochemical Pharmacology, vol. 41, No. 2, pp. 155-162, 1991.

Franz Oesch et al., "Xenobiotic Metabolism," Toxicology, Academic Press, San Diego 1999, pp. 83-109.

* cited by examiner

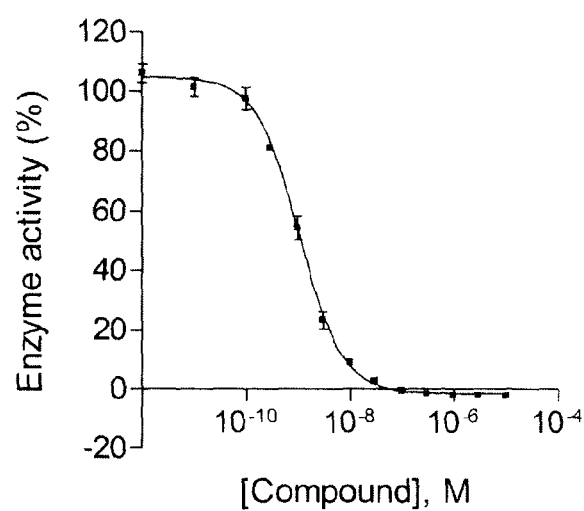

SUBSTITUTED BENZAMIDE DERIVATIVES AS IN VITRO MAO-B INHIBITORS

CROSS-REFERENCE TO RELATED APPLICATIONS

This application is a National Stage of International patent application PCT/BG2014/000027, filed on Jul. 11, 2014, which claims priority to foreign Bulgarian patent application No. BG 111544, filed on Jul. 29, 2013, the disclosures of which are incorporated by reference in their entirety.

TECHNICAL FIELD

The present invention relates to substituted benzamide derivatives, their salts, isomers or mixtures of them applicable as in vitro selective MAO-B inhibitors.

TECHNICAL BACKGROUND

Monoamine oxidases are membrane-bounded flavo-enzymes, which catalyze the oxidative deamination of biogenic amines. Because of their important role in neurotransmitters inactivation, the dysfunction of MAO enzymes (increased levels of MAO activity) is associated with a number of mental and neurological disorders such as depression, anxiety disorders and migraine.

MAO enzymes exist in two isoforms, MAO-A and MAO-B, which have approximately 70% amino acid sequence identity (Oesch and Arand, Toxicology, Academic Press, San Diego USA, 1999) but differ in substrate specificity and tissue distribution (Bach et al., Proc. Natl. Acad. Sci. USA 85, 4934-4938, 1988). MAO-B enzyme is found in high level in the liver, platelets, and especially in brain (Cesura and Pletscher, Prog. Drug Res. 38, 171-297, 1992). The level of MAO-B activity in the brain increases with the age (Fowler et al., J. Neural Transm. 49, 1-20, 1980; Nictora et al., Neurtotoxicology 25, 155-165, 2004; Nagatsu, Neurotoxicology 25, 11-20, 2004.

Natural substrate for MAO-A is serotonin (5-HT) while MAO-B enzyme is elective for 2-phenylethylamine and benzylamine. Dopamine (DA), noradrenaline, adrenaline, tryptamine, and p-tyramine are substrates for both isoformes (Perez et al. *Br. J. Pharmacol.* 127, 869-876, 1999; Youdim et al. *Nat. Rev. Neurosci.* 7, 295-309, 2006). Another important substrate for MAO-B is the Parkinsonism-causing tertiary amine, 1-Methyl-4-phenyl-1,2,3,6-tetrahydropyridine (MPTP), which is metabolized to the active neurotoxin, 1-methyl-4-phenylpyridinium cation ($MPP^+$) in the brain by MAO-B (Youdim et al., *Biochem. Pharmacol.* 41, 155-162, 1991; Petzer et al., *Bioorg. Med. Chem.* 11, 1299-1310, 2003). This finding indicates a causal connection between MAO-B enzymatic activity and Parkinson's disease (Nagatsu, *Neurotoxicology* 25, 11-20, 2004). The process of oxidative deamination of cateholamines, such as dopamine, norepinephrine, and epinephrine, is essential for the correct function of synaptic neurotransmission in the brain (Bortolato et al., *Adv. Drug Deliv. Rev.* 60, 1527-1533, 2008). Furthermore, there are also studies providing the relationship between greater activity of MAO-B and increased cognitive damage of Alzheimer's disease patients (Benedetti and Dostert, *Biochem. Pharmacol.* 38, 555-561, 1989; Emilsson et al., *Neuroscience Lett.* 326, 56-60, 2002). The relationship between oxidative stress and the progressive neuronal impairment indicates that inhibition of MAO-B enzyme activity will have neuroprotective effect, probably by preventing the metabolism of monoamines such as dopamine and other neurotransmitters in the brain.

It is known, that MAO inhibitors (MAOI) are substances that inhibit the MAO activity and due to their selectivity of the MAO enzymes, they can be selective or non-selective. MAO-A inhibitors are therapeutically useful as antidepressants, whereas MAO-B inhibitors can be used in the monotherapy or in combination with levodopa (L-DOPA) for the treatment of Alzheimer's Disease, Parkinson's Disease and other neurological diseases associated with the degeneration of dopaminergic neurons in substantia nigra (Pålhagen et al., *Neurology,* 66, 1200-1206, 2006).

The current therapy of AD and PD is primarily focused on the treatment of the symptoms affecting patient's quality of live. Most of the currently approved medicines are based on dopamine replacement using dopamine-enhancing approach such as levodopa and dopamine agonists that stimulate dopamine production. MAO-B inhibitors are also used as an alternative therapeutic approach for the treatment of neurodegenerative diseases. For example, the irreversible MAO-B inhibitors selegiline (Movergan, Deprenyl, Antiparkin, Xilopar; Riederer and Lachenmayer, *J. Neural Transm.*, 110 (11), 1273-8, 2003) and rasagiline (Azilect; Lakhan, *Molecular Neurodegeneration,* 2(13), 2007) are used as monotherapeutics in early PD and anjuctive therapy to levodopa in late-stage PD. The therapeutic effect of MAO-B inhibitors is associated with the blockage of the oxidative activity of the monoamine oxidase B (MAO-B) enzyme in the brain.

Patent application WO2005/004801 discloses a number of indole, azaindole and related N-substituted piperazine derivatives, wherein the 1H-pyrrolo[2,3-c]pyridine and 1H-pyrrolo[3,2-b]pyridine moieties are attached to the general piperazine unit via an oxalyl spacer. The 1H-pyrrolo[2,3-c]pyridine and 1H-pyrrolo[3,2-b]pyridine moieties do not contain a disubstituted benzamide residue. These compounds are described as antivirals, anti-inflammatory and immunomodulatory activity and are useful in the treatment of HIV/AIDS.

Patent EP0842934 discloses pyrrolo[3,2-b]pyridine derivatives bearing two substituents in the positions 3 and 7. The compounds are potentially useful as $5-HT_{1F}$ agonists for the treatment of migraine.

Patent EP1784404 describes new pirrolo[2,3-c]pyridine derivatives, including as a substituent in the pirrole ring a substituted benzamide and simultaneously a 1,2,3,4-tetrahydroisoguinile group, or substituted such group and substituents at second and third position in the pirrole ring. These substances are used as proton pump inhibitors.

It is therefore an object of the present invention to provide substituted benzamide derivatives, their salts, isomers or mixtures of them, applicable as in vitro selective MAO-B inhibitors for the prevention and treatment of acute and chronic neurological disorders, cognitive and neurodegenerative diseases.

DISCLOSURE OF THE INVENTION

The present invention relates to the use of substituted benzamide derivatives represented by the Formula I:

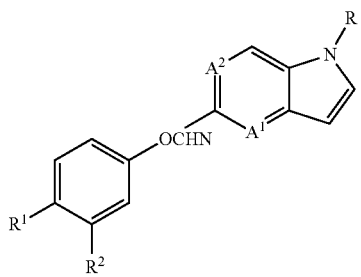

wherein
$A^1$ and $A^2$ are —N or —CH, so that if $A^1$ is —N, then $A^2$ is —CH and if $A^2$ is —N, then $A^1$ is —CH;
R is a hydrogen atom, or represents branched or unbranched —$(C_1$-$C_3)$-alkyl, —$(C_1$-$C_3)$-alkyl, wherein one, two or three hydrogen atoms may be substituted by a halogen or hydroxyl, —$(C_1$-$C_3)$—O—$(C_1$-$C_3)$, —$(C_1$-$C_3)$—O—$(C_1$-$C_3)$, wherein one, two or three hydrogen atoms may be substituted by a halogen, or R is a group

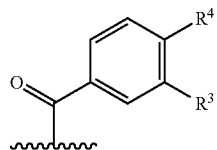

wherein $R^3$ and $R^4$ both together or independently are halogen, hydroxyl, —$(C_1$-$C_3)$-alkyl, —$(C_1$-$C_3)$-alkyl, wherein one, two or three hydrogen atoms may be substituted by a halogen or hydroxyl, —O—$(C_1$-$C_3)$-alkyl, —O—$(C_1$-$C_3)$-alkyl, wherein one, two or three hydrogen atoms may be substituted by a halogen, —O—$(C_1$-$C_3)$—O—$(C_1$-$C_3)$, —O—$(C_1$-$C_3)$—O—$(C_1$-$C_3)$, wherein one, two or three hydrogen atoms may be substituted by a halogen;

and wherein $R^1$ and $R^2$ both together or independently are halogen, hydroxyl, —$(C_1$-$C_3)$-alkyl, —$(C_1$-$C_3)$-alkyl, wherein one, two or three hydrogen atoms may be substituted by a halogen or hydroxyl, —O—$(C_1$-$C_3)$-alkyl, —O—$(C_1$-$C_3)$-alkyl, wherein one, two or three hydrogen atoms may be substituted by a halogen, —O—$(C_1$-$C_3)$—O—$(C_1$-$C_3)$, —O—$(C_1$-$C_3)$—O—$(C_1$-$C_3)$, wherein one, two or three hydrogen atoms may be substituted by a halogen, and their pharmaceutically acceptable salts, isomers or mixtures thereof as in vitro selective MAO-B inhibitors. More precisely, the substituted benzamide derivatives of Formula I, their pharmaceutically acceptable salts, isomers or mixtures thereof are useful for the manufacture of a medicament for prevention and treatment of acute and chronic neurological disorders, cognitive and neurodegenerative diseases. Especially, the compounds of Formula I, their pharmaceutically acceptable salts, isomers or mixtures thereof are useful for prevention and treatment of neurodegenerative disorders such as Parkinson's Disease and Alzheimer's Disease.

According to one preferred embodiment of the present invention, for the manufacturing of a medicament for prevention and treatment of acute and chronic neurological disorders, cognitive and neurodegenerative diseases are used compounds of Formula I, selected from the group consisting of:

3,4-dichloro-N-(1H-pyrrolo[3,2-]pyridin-5-yl)benzamide,
3-chloro-4-fluoro-N-(1H-pyrrolo[3,2-b]pyridin-5-yl)benzamide,
4-chloro-3-fluoro-N-(1H-pyrrolo[3,2-b]pyridin-5-yl)benzamide,
3,4-difluoro-N-(1H-pyrrolo[3,2-b]pyridin-5-yl)benzamide,
4-chloro-N-(1-(4-chloro-3-fluorobenzoyl)-1H-pyrrolo[3,2-b]pyridin-5-yl)-3-fluorobenzamide,
3,4-dichloro-N-(1H-pyrrolo[2,3-c]pyridin-5-yl)benzamide,
3-chloro-4-fluoro-N-(1H-pyrrolo[2,3-c]pyridin-5-yl)benzamide,
3,4-difluoro-N-(1H-pyrrolo[2,3-c]pyridin-5-yl)benzamide,
and their pharmaceutically acceptable salts, isomers or mixtures thereof.

The compounds selected from the Formula I of the present invention can be radiolabeled, for example, with tritium. Such radiolabeled analogues are within the scope of the present invention and may also be useful as pharmacological tools, e.g., as radioligands in the MAO inhibitory studies.

The compounds of Formula I are prepared by a process well known in the art. According to one preferred embodiment, the compounds of the present invention are prepared by reacting of 1H-pyrrolo[3,2-b]pyridin-5-amine ($A^2$ is —CH) or 1H-pyrrolo[2,3-c]pyridin-5-amine ($A^1$ is —CH) of Formula II with a suitable electrophile such as substituted benzoyl chlorides of Formula III following the synthetic procedure showed in Scheme 1:

Scheme I

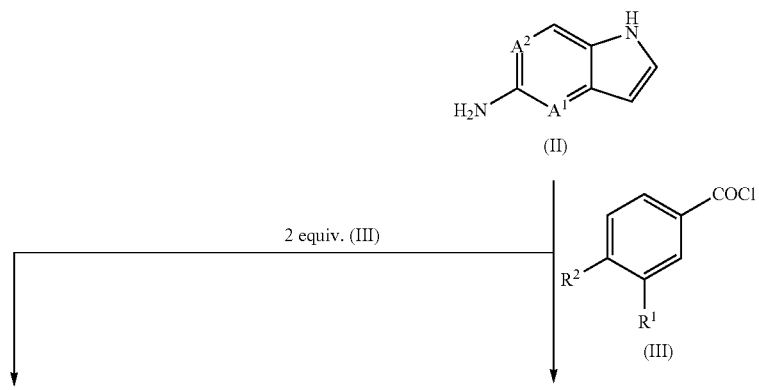

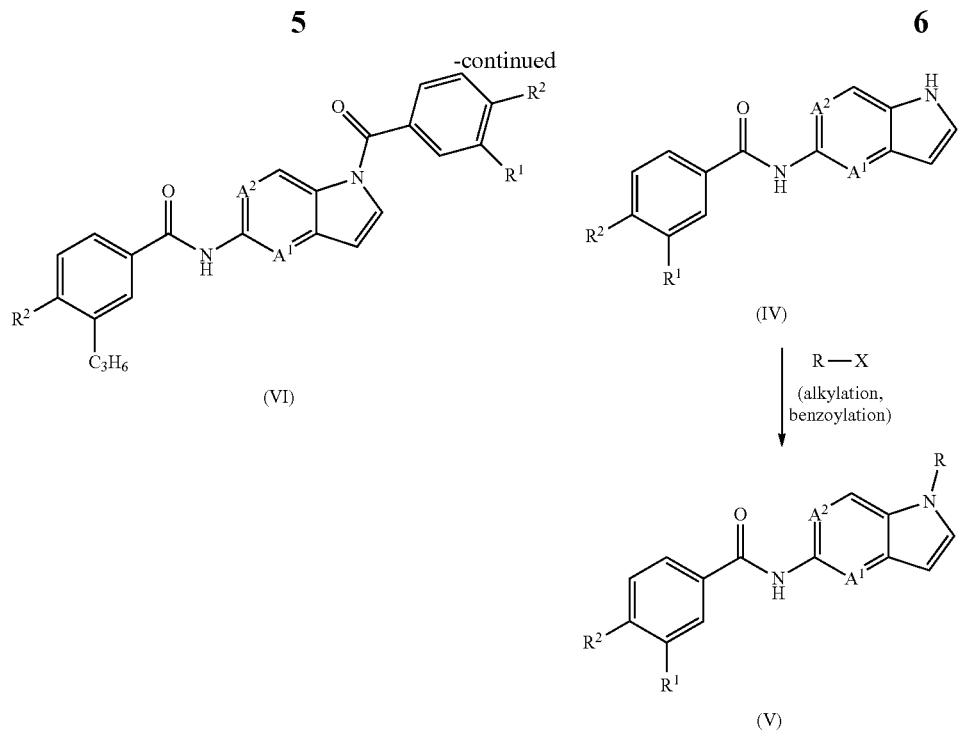

wherein $A^1$, $A^2$, R, $R^1$ and $R^2$ are as previously described.

The synthesis of 1H-pyrrolo[3,2-b]pyridin-5-amine ($A^2$ is —CH) or 1H-pyrrolo[2,3-c]pyridin-5-amine ($A^1$ is —CH) of Formula II is carried out by methods well known in the art, e.g. similarly to the process described in the literature (Filla, S. A.; Schaus, J. M.; Phebus, L. A.; Johnson, K. W.; Patent EP0842934; Fila et al., *J. Med. Chem.* 46. 3060-3071, 2003). According to the three-step synthetic procedure described herein, as a starting materials are used the commercially available (Aldrich) 2-amino-6-methyl-5-nitropyridine and 2-amino-4-methyl-5-nitropyridine.

As showed in Scheme 1, an amide bond is formed by reaction of the differently substituted benzoyl chlorides of general Formula III with the amino group of the corresponding 1H-pyrrolo[3,2-b]pyridin-5-amine ($A^2$ is —CH) or 1H-pyrrolo[2,3-c]pyridin-5-amine ($A^2$ is —CH) of general Formula II. The amide coupling reaction leading to the formation of compounds of Formula IV can be conducted at room temperature in the presence of a suitable base such as pyridine. The complete conversion of the starting material was monitored by TLC or by high performance liquid chromatography (HPLC) coupled to an UV-detector and to electrospray ionization mass spectrometer (ESI-MS).

Intermediates of Formula IV, wherein R is hydrogen, can be defined as final compounds related to general Formula I. The compounds of Formula IV can be also useful intermediates for the preparation of compounds of Formula V, wherein R is different than hydrogen. Typically, the conversion is accomplished under standard conditions, for example, an alkylation or acylation (benzoylation) reaction under basic conditions. To introduce an additional substituent in the compounds of general Formula IV, the intermediates of Formula IV can be alkylated with an appropriate alkylating reagent such as alkylhalide (where X is a bromine, chlorine or iodine) or methyl methanesulfonate (MMS), when R is a methyl group. The reaction is conducted at room temperature in the presence of a base such as potassium carbonate or another suitable base in an appropriate solvent such as N,N-dimethylformamide (DMF). Depending on the alkylating reagent, the reaction can be achieved at temperatures between 60° C. and 90° C. until complete conversion of the starting material.

According to the alkylation step described above, compounds selected from the Formula I of the present invention can be radiolabeled, for example, by an alkylation reaction with the corresponding radiolabeled alkylating reagent, e.g. methylation with tritium-labeled methyl methanesulfonate [$^3$H]MMS.

In particular, the radiolabeled compounds of Formula I may also be useful as pharmacological tools, e.g., as radioligands for in vitro and in vivo studies, including diagnostics for positron emission tomography (PET).

Optionally, as shown in Scheme I, compounds of Formula VI are prepared from the corresponding intermediates of Formula IV following well-known procedures (e.g., Ghosh and Das, *Org. Chem Int., Vol.* 2010, 1-3, 2010) by a benzoylation reaction using differently substituted benzoyl chlorides.

In accordance with the present invention wherein $A^1$, $A^2$, R, $R^1$, and $R^2$ are defined as mentioned above, the N-benzoyl-substituted compounds of the Formula VI can optionally be prepared via intermediates of Formula IV, as shown in Scheme 1. This step is performed in analogy to the amide coupling reaction to form compounds of Formula IV by using of excess of the corresponding benzoyl chloride. More precisely (preferably), the reaction can be performed in the presence of two equivalents of benzoyl chloride at room or elevated temperature. The final compounds were purified by column chromatography on silica gel followed by a preparative reverse phase HPLC.

According to another preferred embodiment of the present invention, the prodrugs of the compounds of Formula I are used as in vitro selective MAO-B inhibitors for the manufacture of a medicament for the prevention and treatment of acute and chronic neurological disorders, cognitive and neurodegenerative diseases. Such a prodrug is a compound of formula IV, which is administered as a N-alkyl(methyl, ethyl or propyl)phosphate disodium or dipotassium salt, di-tert-butyl N-alkyl(methyl, ethyl or propyl)phosphate, or as a N-methyl pivalate. These prodrugs are useful to afford the transmittal across a cell membrane where water solubility is determinant to drug mobility, but then inside the cell are metabolically hydrolysed to the dealkylated biologically active compounds.

According to still another preferred embodiment, the present invention relates to the use of the pharmaceutically acceptable salts of the compounds presented in Formula I as in vitro selective MAO-B inhibitors for the manufacture of a medicament for the prevention and treatment of acute and chronic neurological disorders, cognitive and neurodegenerative diseases are. Such salts include, but are not limited to organic acids such as trifluoroacetic acid, acetic acid, oxalic acid, lactonic acid, fumaric acid, benzenesulfonic acid, D- or L-malic acid, maleic acid, methanesulfonic acid, ethanesulfonic acid, p-toluenesulfonic acid, salicylic acid, tartaric acid, citric acid, succinic acid, malone acid, ascorbic acid or lysine acid and the like, or inorganic acids, such as hydrochloric acid, hydrobromic acid, nitric acid, sulphuric acid, perchloric acid, phosphoric acid or metaphosphoric acid and the like, more preferably hydrochloric acid, trifluoroacetic acid or acetic acid.

Another preferred embodiment of the invention include pharmaceutically acceptable salts of the compounds represented by the Formula I formed when an acidic proton (e.g., NH-group) present in the parent compound either is replaced by a metal ion such as an alkali ion, like sodium or potassium, an alkaline earth ion, such as calcium or magnesium ion; or coordinates with an organic base such as monoethanolamine, diethanolamine, triethanolamine, diethylamine, triethylamine, N-methylglucamine, and the like.

Since the MAO-B is highly expressed in brain, e.g. in glial cells in the substantia nigra, compounds of the present invention are useful for treatment, prevention, or diagnosis of CNS disorders such as neuroinflammatory conditions and diseases such as neurodegenerative diseases (e.g., Alzheimer's and Parkinson's disease), catalepsy, dystonia, dyskinetic syndrome, restless legs syndrome, migraine, or dementia, and may have neuroprotective effects.

The neuroprotective effect of the compounds of the present invention is revealed by blockage of the production of hydrogen peroxide and other reactive (neurotoxic) oxygen species (ROS), which contribute to oxidative stress and neuronal cell damage and by prevention of the catabolic degradation of dopamine transmitter in the human brain.

The MAO-A and MAO-B enzyme activity of the compounds, according to the present invention, was estimated following an assay adapted from the method described by Holt et al. (*Anal. Biochem.* 244, 384-392, 1997). The MAO experiments were performed using a fluorescence-based detection of resorufin, obtained by a reaction of released from the biological sample hydrogen peroxide with 10-acetyl-3,7-dihydroxyphenoxazine (ADHP) in the presence of a peroxidase (horseradish peroxidase-coupled reaction, HRP). The inhibitory in vitro MAO activity of the compounds of general Formula I was investigated at rat and human MAO-A and MAO-B. To perform rat MAO-A and MAO-B experiments, a preliminary membrane preparation of mitochondrial-enriched rat livers isolated from male Sprague-Dawley rats (Harlan Sprague Dawley, Dublin, US) was required. As sources for recombinant human MAO-A and MAO-B enzymes were used microsomal products, prepared from baculovirus-infected insect cells expressing human MAO-A (Sigma-Aldrich, M7316) and human MAO-B (Sigma-Aldrich, M7441), respectively.

To estimate MAO inhibitory activity of the compounds of Formula I at rat and human MAO-A and MAO-B, the corresponding test compound was dissolved in 100% DMSO and subsequently added to the appropriate enzyme solution containing rat liver mitochondria (rat MAO-A and -B) or recombinant human protein (for determination of human MAO-A and -B) in sodium phosphate buffer. The test sample was incubated for 30 min at room temperature prior to the addition of Amplex Red reagent (Invitrogen A12214) using for the fluorescence-based measuring of MAO inhibitory activity. The enzymatic reaction was started by the addition of the substrate p-tyramine. The fluorescence measurements were performed over a period of 45 min using a microplate fluorescence reader (excitation at 544 nm and emission at 590 nm). $IC_{50}$ values were determined from the inhibition curves obtained using different inhibitor concentrations in triplicate within the same experiment. A four-parameter logistic equation was used to fit the dose-response curves for test compounds using a computer program.

The compounds of general Formula I according to the present invention or their pharmaceutically acceptable salts, isomers or mixtures thereof have MAO-B inhibitory activity and are applicable as active substances in the pharmaceutical preparations for oral and parenteral use, e.g., as medicaments in the form of pharmaceutical compositions. The pharmaceutical compositions can be administered in the form of capsules or tablets, gel or liquid dosage forms, prepared in a known manner by means of common pharmaceutically acceptable carriers and/or excipients.

FIGURES

FIG. 1 represents the inhibition curve for 3,4-dichloro-N-(1H-pyrrolo[3,2-b]pyridin-5-yl)benzamide vs. human recombinant MAO-B enzyme.

EXAMPLES

The following Examples are provided to illustrate the methods for preparation and functional assays for determination of the pharmacological effect of the compounds of Formula I according to the present invention. They should not be considered as limiting the scope of the present invention, but merely as being representative thereof.

Example 1

Preparation of 3,4-dichloro-N-(1H-pyrrolo[3,2-b]pyridin-5-yl)benzamide

A solution of 1H-pyrrolo[3,2-b]pyridin-5-amine (155.8 mg, 1.17 mmol) in pyridine (3.0 mL) was treated with 3,4-dichlorobenzoyl chloride (245.1 mg, 1.17 mmol) and the reaction mixture stirred at room temperature until complete conversion could be detected by TLC control (eluent: dichloromethane/methanol, 9:1, v/v). The mixture was concentrated in vacuo and the residue treated with water (10 mL). The precipitate formed was filtered under reduced pressure and purified by column chromatography on silica gel (eluent: dichloromethane/methanol, 9:1, v/v, $R_f$=0.81) to give 230 mg (64%) of the title compound as a slight yellowish solid, m.p. 197.7-199.1° C. $^1$H NMR (500 MHz, DMSO-$d_6$) δ (ppm): 6.46 (t, J=1.89 Hz, 1H), 7.61 (t, J=2.84 Hz, 1H), 7.77 (d, J=8.19 Hz, 1H), 7.83 (dd, J=0.63 and 8.83 Hz, 1H), 7.92 (d, J=8.51 Hz, 1H), 8.01 (dd, J=1.89 and 8.2

Hz, 1H), 8.29 (d, J=1.89 Hz, 1H), 10.8 (s, 1H), 11.3 (s, 1H). $^{13}$C NMR (125 MHz, DMSO-d$_6$) δ (ppm): 100.8, 109.3, 120.3, 126.3, 128.2, 129.7, 130.0, 130.7, 131.4, 134.5, 135.1, 143.9, 145.9, 163.3. LC/ESI-MS m/z: negative mode 304 ([M−H]$^−$), positive mode 306 ([M+H]$^+$)

Example 2

Preparation of 3-chloro-4-fluoro-N-(1H-pyrrolo[3,2-b]pyridin-5-yl)benzamide

The compound was prepared in a similar manner as Example 1 starting with 1H-pyrrolo[3,2-b]pyridin-5-amine (151.8 mg, 1.14 mmol) and 3-chloro-4-fluorobenzoyl chloride (220 mg, 1.14 mmol). Purification was performed by column chromatography on silica gel (eluent: dichloromethane/methanol, 9:1, v/v, R$_f$=0.72) to provide 135 mg (41%) as a white solid, m.p. 170.7-171.7° C. $^1$H NMR (500 MHz, DMSO-d$_6$) δ (ppm): 6.44-6.47 (m, 1H), 7.54 (t, J=8.82 Hz, 1H), 7.61 (t, J=3.15 Hz, 1H), 7.83 (dd, J=0.63/8.83 Hz, 1H), 7.92 (d, J=8.83 Hz, 1H), 8.07 (ddd, J=2.20/4.73/8.51 Hz, 1H), 8.28 (dd, J=2.20/6.93 Hz, 1H), 10.75 (s, 1H), 11.29 (s, 1H). $^{13}$C NMR (125 MHz, DMSO-d$_6$) δ (ppm): 100.8, 109.3, 117.0 (d, J=21.44 Hz), 119.8 (d, J=17.95 Hz), 120.3, 126.3, 129.2 (d, J=8.22 Hz), 129.6, 130.6, 132.4 (d, J=3.49 Hz), 143.9, 146.0, 159.3 (d, J=251.57 Hz), 163.2. LC/ESI-MS m/z: negative mode 288 ([M−H]$^−$), positive mode 290 ([M+H]$^+$).

Example 3

Preparation of 4-chloro-3-fluoro-N-(1H-pyrrolo[3,2-b]pyridin-5-yl)benzamide

The compound was prepared in a similar manner as Example 1 starting with 1H-pyrrolo[3,2-b]pyridin-5-amine (275.6 mg, 2.07 mmol) and 4-chloro-3-fluorobenzoyl chloride (400 mg, 2.07 mmol) except using of additionally purification by preparative reverse phase HPLC. Purification was performed by column chromatography on silica gel (eluent: dichloromethane/methanol, 9:1, v/v, R$_f$=0.63) following by preparative reverse phase HPLC (solvents: methanol (% B)/water (% A), 70:30) to provide 228 mg (38%) as a white solid, m.p. 145.6-146.6° C. $^1$H NMR (500 MHz, DMSO-d$_6$) δ (ppm): 6.46 (sept, J=0.63 Hz, 1H), 7.61 (t, J=3.15 Hz, 1H), 7.73 (dd, J=7.57/8.20 Hz, 1H), 7.83 (dd, J=0.95/8.83 Hz, 1H), 7.91 (ddd, J=0.63/2.21/8.20 Hz, 1H), 7.92 (d, J=8.83 Hz, 1H), 8.07 (dd, J=2.20/100.8, 109.3, 116.4 (d, J=22.69 Hz), 120.3, 123.1 (d, J=17.7 Hz), 125.3 (d, J=3.24 Hz), 126.3, 129.7, 130.8, 135.7 (d, J=5.98 Hz), 143.9, 145.9, 157.0 (d, J=247.08 Hz), 163.3. LC/ESI-MS m/z: negative mode 288 ([M−H]$^−$), positive mode 290 ([M+H]$^+$).

Preparative Reverse Phase HPLC Separation Method

The preparative sample containing the compound of Example 3 was purified using Eurospher 100-10 C18 column (250×20 mm, 10 μm particle size, flowrate=20.0 mL/min) from Knauer (Berlin, Germany) equipped with a preparative pump 1800 from Knauer Smartline and an UV detector in the range from 220 to 400 nm. The gradient remains isocratic (% Sol. B (methanol)=70, % Sol. A (water)=30) for 20 min.

Example 4

Preparation of 3,4-difluoro-N-(1H-pyrrolo[3,2-b]pyridin-5-yl)benzamide

The compound was prepared in a similar manner as Example 3 starting with 1H-pyrrolo[3,2-b]pyridin-5-amine (155.8 mg, 1.17 mmol) and 3,4-difluorobenzoyl chloride (206.6 mg, 1.17 mmol). Purification of the product was performed by column chromatography on silica gel (eluent: dichloromethane/methanol, 9:1, v/v, R$_f$=0.61) following by preparative reverse phase HPLC (solvents: methanol (% B)/water (% A), 70:30) to provide 95.6 mg (30%) as a white solid, m.p. 101.5-102.5° C. $^1$H NMR (500 MHz, DMSO-d$_6$) δ (ppm): 6.45-6.47 (m, 1H), 7.57 (ddd, J=5.99/8.51/10.72 Hz, 1H), 7.61 (t, J=2.83 Hz, 1H), 7.83 (dd, J=0.63/8.83 Hz, 1H), 7.91 (d, J=8.83 Hz, 1H), 7.92-7.97 (m, 1H), 8.13 (ddd, J=2.21/7.57/11.67 Hz, 1H), 10.71 (s, 1H), 11.30 (s, 1H). $^{13}$C NMR (125 MHz, DMSO-d$_6$) δ (ppm): 100.7, 109.3, 117.5 (dd, J=17.45/29.67 Hz), 120.3, 125.6 (dd, J=3.99/6.48 Hz), 126.3, 129.6, 132.1 (d, J=3.49 Hz), 143.9, 146.0, 150.4 (dd, J=12.72/64.58 Hz), 152.7, 163.2. LC/ESI-MS m/z: negative mode 272 ([M−H]$^−$), positive mode 274 ([M+H]$^+$).

Example 5

Preparation of 4-chloro-N-(1-(4-chloro-3-fluorobenzoyl)-1H-pyrrolo[3,2-b]pyridin-5-yl)-3-fluorobenzamide The compound was prepared in a similar manner as Example 3 starting with 1H-pyrrolo[3,2-b]pyridin-5-amine (137.8 mg, 1.03 mmol) and an excess of 4-chloro-3-fluorobenzoyl chloride (400 mg, 2.07 mmol). Purification of product was performed by column chromatography on silica gel (eluent: dichloromethane/methanol, 9:1, v/v, R$_f$=0.96) following by preparative reverse phase HPLC (solvents: methanol (% B)/water (% A), 70:30) to provide 131 mg (28%) as a white solid, m.p. 206.2-207.2° C. $^1$H NMR (500 MHz, DMSO-d$_6$) δ (ppm): 6.79 (dd, J=0.63/3.78 Hz, 1H), 7.66 (ddd, J=0.63/2.21/8.20 Hz, 1H), 7.75 (dd, J=7.56/8.19 Hz, 1H), 7.79 (d, J=2.78 Hz, 1H), 7.85 (t, J=8.20 Hz, 1H), 7.90 (dd, J=1.89/9.46 Hz, 1H), 7.93 (dd, J=1.58/7.57 Hz, 1H), 8.09 (dd, J=1.90/10.09 Hz, 1H), 8.21 (d, J=9.14 Hz, 1H), 8.58 (d, J=8.83 Hz, 1H), 11.08 (s, 1H). $^{13}$C NMR (125 MHz, DMSO-d$_6$) δ (ppm): 108.5, 111.6, 116.5 (d, J=22.69 Hz), 117.9 (d, J=23.19 Hz), 123.4 (d, J=17.46 Hz), 123.9 (d, J=17.45 Hz), 125.1, 125.5 (d, J=3.49 Hz), 126.3, 126.6 (d, J=3.49 Hz), 130.9, 131.4, 132.4, 134.0 (d, J=6.73 Hz), 135.2 (d, J=6.23 Hz), 147.2, 149.3, 157.0 (d, J=247.33 Hz), 157.1 (d, J=248.57 Hz), 163.8, 166.0. LC/ESI-MS m/z: negative mode 444 ([M−H]$^−$), positive mode 446 ([M+H]$^+$).

Example 6

Preparation of 3,4-dichloro-N-(1H-pyrrolo[2,3-c]pyridin-5-yl)benzamide

The compound was prepared in a similar manner as Example 1 starting with 1H-pyrrolo[2,3-c]pyridin-5-amine (115.8 mg, 0.87 mmol) and 3,4-dichlorobenzoyl chloride (182.2 mg, 0.87 mmol). The crude product was purified by column chromatography on silica gel (eluent: dichloromethane/methanol, 9:1, v/v, R$_f$=0.52) to provide 119.3 mg (45%) as a white solid, m.p. 202.3-203.3° C. $^1$H NMR (500 MHz, DMSO-d$_6$) δ (ppm): 6.51-6.52 (m, 1H), 7.60 (t, J=2.84 Hz, 1H), 7.77 (d, J=8.52 Hz, 1H), 7.87 (d, J=8.19 Hz, 1H), 8.00 (dd, J=2.2/8.51 Hz, 1H), 8.28 (s, 1H), 8.55 (s, 1H), 10.66 (s, 1H), 11.51 (s, 1H). $^{13}$C NMR (125 MHz, DMSO-d$_6$) δ (ppm): 101.0, 105.3, 128.2, 129.3, 129.9, 130.7, 130.8, 131.3, 131.9, 134.1, 135.6, 142.6, 162.6. LC/ESI-MS m/z: negative mode 304 ([M−H]$^−$), positive mode 306 ([M+H]$^+$).

Example 7

Preparation of 3-chloro-4-fluoro-N-(1H-pyrrolo[2,3-c]pyridin-5-yl)benzamide

The compound was prepared in a similar manner as Example 1 starting with 1H-pyrrolo[2,3-c]pyridin-5-amine (94.5 mg, 0.71 mmol) and 3-chloro-4-fluorobenzoyl chloride (137 mg, 0.71 mmol). The crude product was purified by column chromatography on silica gel (eluent: dichloromethane/methanol, 9:1, v/v, $R_f$=0.46) to provide 82.5 mg (40%) as a yellowish solid, m.p. 205.8-206.8° C. $^1$H NMR (500 MHz, DMSO-$d_6$) δ (ppm): 6.54 (sept, J=0.95 Hz, 1H), 7.54 (t, J=8.82 Hz, 1H), 7.60 (t, J=2.52 Hz, 1H), 8.06 (ddd, J=2.21/4.73/8.51 Hz, 1H), 8.27 (dd, J=2.21/7.26 Hz, 1H), 8.28 (s, 1H), 8.55 (s, 1H), 10.60 (s, 1H), 11.50 (s, 1H). $^{13}$C NMR (125 MHz, DMSO-$d_6$) δ (ppm): 100.9, 105.3, 116.9 (d, J=21.44 Hz), 119.7 (d, J=17.95 Hz), 129.2 (d, J=8.23 Hz), 130.5, 130.8, 131.3, 131.9, 132.5 (d, J=3.24 Hz), 134.1, 142.7, 159.2 (d, J=251.32 Hz), 162.9. LC/ESI-MS m/z: negative mode 288 ([M−H]$^-$), positive mode 290 ([M+H]$^+$).

Example 8

Preparation of 3,4-difluoro-N-(1H-pyrrolo[2,3-c]pyridin-5-yl)benzamide

The compound was prepared in a similar manner as Example 3 starting with 1H-pyrrolo[2,3-c]pyridin-5-amine (66.6 mg, 0.50 mmol) and 3,4-difluorobenzoyl chloride (88.3 mg, 0.50 mmol). Purification of the product was performed by column chromatography on silica gel (eluent: dichloromethane/methanol, 9:1, v/v, $R_f$=0.55) following by preparative reverse phase HPLC (solvents: methanol (% B)/water (% A), 70:30) to provide 70 mg (51%) as a white solid, m.p. 209.8-211.8° C. $^1$H NMR (500 MHz, DMSO-$d_6$) δ (ppm): 6.50-6.51 (m, 1H), 7.56 (ddd, J=5.99/8.51/10.72 Hz, 1H), 7.61 (t, J=2.84 Hz, 1H), 7.91-7.96 (m, 1H), 8.11 (ddd, J=2.2/7.88/11.66 Hz, 1H), 8.28 (s, 1H), 8.55 (s, 1H), 10.56 (s, 1H), 11.50 (s, 1H). $^{13}$C NMR (125 MHz, DMSO-$d_6$) δ (ppm): 101.0, 105.3, 117.5 (dd, J=17.45/29.67 Hz), 125.5 (d, J=3.99 Hz), 130.8, 131.3, 131.9, 132.3, 134.1, 142.7, 148.3, 150.4 (dd, J=12.46/52.85 Hz), 152.5, 162.94. LC/ESI-MS m/z: negative mode 272 ([M−H]$^-$), positive mode 274 ([M+H]$^+$).

In Table 1 are presented the compounds of Examples 1-8 obtained according to the synthetic procedures of the present invention. Their structures, melting points and molecular weights are reported.

TABLE 1

| EXAMPLE | M. p. (° C.) | MW |
|---|---|---|
| 1 | 197-200 | 306.2 |
| 2 | 170-172 | 289.7 |
| 3 | 145-146 | 289.7 |
| 4 | 101-103 | 273.2 |
| 5 | 206-207 | 446.24 |
| 6 | 202-204 | 306.2 |

TABLE 1-continued

| EXAMPLE | M. p. (° C.) | MW |
|---|---|---|
| 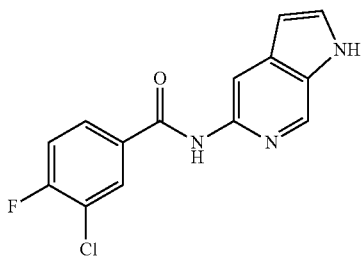 7 | 205-207 | 289.7 |
| 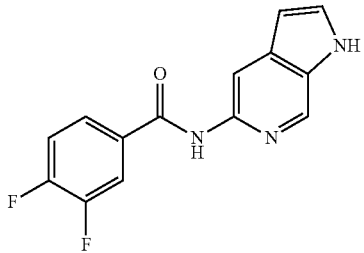 8 | 209-212 | 273.2 |

Example 9

Pharmacological Activity of the Compounds of Formula I was Tested Using the Following Biological Experiments In Vitro MAO-A and MAO-B Enzyme Activities Assay MAO-A and MAO-B enzymatic activity of the compounds was measured in 96-well-plates using a continuous fluorescence-based assay. This assay was adapted from the method described by Holt et al. (*Anal. Biochem.*, 244, 384-392, 1997). The MAO experiments were performed using the commercial assay kit Amplex Red (Invitrogen A12214). The kit was stored frozen at ≤−20° C. and protected from light before use. The Amplex Red MAO assay kit was used for the detection of $H_2O_2$ released from the biological sample. Subsequently, a reaction of 10-acetyl-3, 7-dihydroxyphenoxazine (ADHP, Amplex Red reagent) with $H_2O_2$ in the presence of a peroxidase (horse-radish peroxidase-coupled reaction, HRP) led to the production of resorufin. The quantification of hydrogen peroxide released from the biological sample and the subsequent production of resorufin was monitored using a fluorescence microplate reader (Holt et al., *Anal. Biochem.*, 244, 384-392, 1997). To ensure an optimal efficiency of the Amplex Red reagent, the MAO assay's were performed at pH 7.4.

Membrane Preparation of Rat Liver Mitochondria

MAO enzyme-containing mitochondrial-enriched fractions of rat were obtained from male Sprague-Dawley rat livers (250-300 g, Harlan Sprague-Dawley, Dublin, Va., US). The livers (10.0 g) were dissected, given into 15.0 mL of an ice-cold 5.0 mM Hepes buffer (pH 7.4), containing 210 mM mannitol, 70 mM sucrose, 0.5 mM ethylene glycoltetraacetic acid (EGTA), and 2.0 mg/mL of bovine serum albumin (BSA), and homogenized using a glass/Teflon potter (10 ups and downs at 1100 rpm). After homogenization, the volume is adjusted to 100 mL with the same buffer. After a low speed centrifugation (10 min at 600 g; 4° C.), the supernatant was further centrifuged at 15,000 rpm for 5 min at +4° C. The resulting pellet was resuspended in 2.0 mL of a 50 mM sodium phosphate buffer (pH 7.4) and stored at −80° C. in aliquots of 1.0 mL until further use.

Rat MAO-A Assay

Assays were performed in 96-well plates in a final volume of 200 µL at room temperature. Rat liver mitochondria samples were pretreated for 15 min at room temperature with an aqueous solution of deprenyl (300 nM) to irreversibly inhibit MAO-B activity. Test compounds (2.0 µL), dissolved in DMSO (100%), were added to 90.0 µL of mitochondrial preparation (25.0 µg prot) and incubated for 30 min prior to the addition of 90 µL of freshly prepared Amplex Red reagent, prepared as recommended in the kit from Invitrogen (A12214). For a 96-well plate, 1.0 mg of Amplex Red, dissolved in 200 µL of DMSO (100%) and 100 µL of reconstituted horse-radish peroxidase (HRP 200 U/mL, Sigma Aldrich P6782) stock solution (kit vial+1.0 mL of sodium phosphate buffer) were added to 9700 µL of sodium phosphate buffer (250 mM at pH 7.4). The enzymatic reaction was started by the addition of 20 µL/well of an aqueous solution (300 µM final concentration) of the substrate p-tyramine (Alfa Aesar A12220). Fluorescence measurements were performed for 45 min using a microplate fluorescence reader (excitation at 544 nm and emission at 590 nm). Clorgyline (1.0 µM) from Sigma Aldrich (M3778) was used to determine the non-MAO-A enzyme activity and serves as a positive control.

Rat MAO-B Assay

Assays were performed as described for MAO-A except that mitochondrial-enriched rat liver samples were pretreated with clorgyline (30 nM) to irreversibly inhibit the MAO-A activity; 5.0 µg prot/assay were used instead of 25.0 µg for MAO-A. The non-MAO-B enzyme activity was determined in the presence of deprenyl (1.0 µM) and serves as a positive control.

Human MAO-A Assay

Recombinant human MAO-A enzyme, expressed in baculovirus-infected insect cells, was purchased from Sigma-Aldrich (M7316). The assay was carried out in 96-well plates in a final volume of 200 µL at room temperature. According to the experiment protocol, a solution of test compound (2.0 µL) in DMSO (100%) was added to 90.0 µL of protein solution (0.3 µg prot/well, containing 6.6 µL protein and 9.993 µL phosphate buffer) and incubated for 30 min prior to the addition of 90 µL of freshly prepared Amplex Red reagent. The Amplex Red reagent was prepared as described for rat MAO-A. The enzymatic reaction was started by the addition of 20.0 µL/well of an aqueous solution of the substrate p-tyramine (150 µM final concentration). The p-tyramine solution was prepared from p-tyramine hydrochloride (45 µL) in water (100 mM) and phosphate buffer (2955 µL). Fluorescence measurements were performed for 45 min and the concentration-response curve of clorgyline (1.0 µL) serves as a positive control. DMSO (2.0 µL) was used as a negative control.

Human MAO-B Assay

Recombinant human MAO-B enzyme, expressed in baculovirus-infected insect cells, was purchased from Sigma-Aldrich (M7441). The assay was performed as described for human MAO-A except that deprenyl (1.0 µL) was used as a positive control; 90.0 µL protein suspension for MAO-B contains 20.0 µL protein and 9,980 mL buffer (0.9 µg prot/well).

As shown in Table 2, the compounds of Examples 1-7 of the present invention are selective and highly potent inhibitors at rat and human MAO-B with $IC_{50}$ values in the nanomolar range. The compound numbers in Table 2 are the same that in the preparative Examples above.

The results of the functional investigation done regarding inhibitory activity for Compound 1 of Table 2 above, 3,4-dichloro-N-(1H-pyrrolo[3,2-b]pyridin-5-yl) benzamide, vs. human recombinant MAO-B (hMAO-B) enzyme are shown on FIG. 1. The estimated $IC_{50}$ (p-tyramine 150 μM) is 1.13±0.16 nM.

TABLE 2

| EXAMPLE/COMPOUND | rat MAO-A (rat liver mitochondria) $IC_{50}$ (nM) | rat MAO-B (rat liver mitochondria) $IC_{50}$ (nM) | human MAO-A $IC_{50}$ (nM) | human MAO-B $IC_{50}$ (nM) |
|---|---|---|---|---|
| 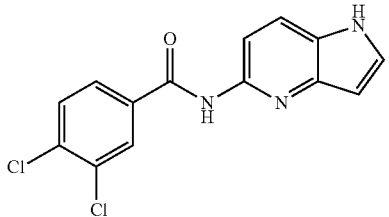 1 | >10000 | 4.20 ± 0.97 | >10000 | 1.13 ± 0.16 |
| 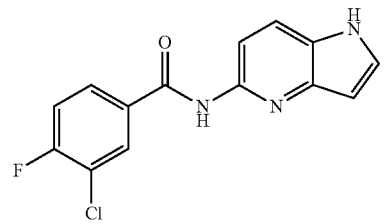 2 | >10000 | 4.90 ± 0.33 | >10000 | 3.27 ± 0.04 |
| 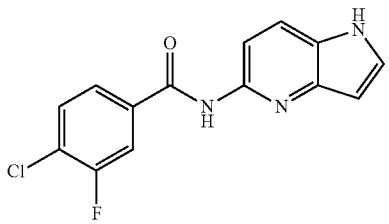 3 | >10000 | 85.5 ± 5.8 | >10000 | 10.9 ± 0.75 |
| 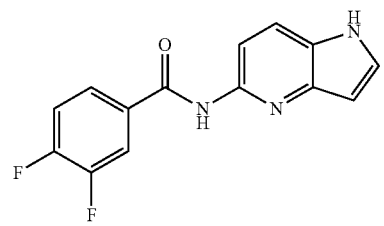 4 | >10000 | 153 ± 11 | >10000 | 46.1 ± 1.5 |
| 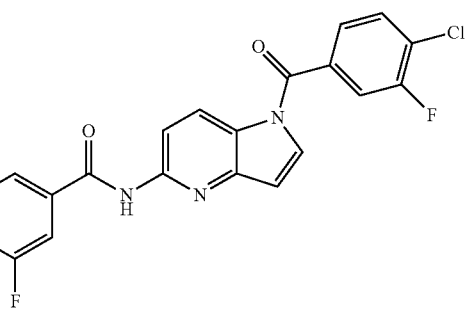 5 | >10000 | 246 ± 53 | >10000 | 27.5 ± 2.0 |

TABLE 2-continued

| EXAMPLE/COMPOUND | rat MAO-A (rat liver mitochondria) IC$_{50}$ (nM) | rat MAO-B (rat liver mitochondria) IC$_{50}$ (nM) | human MAO-A IC$_{50}$ (nM) | human MAO-B IC$_{50}$ (nM) |
|---|---|---|---|---|
| 6 | ≥10000 | 224 ± 17 | <10000 | 28.5 ± 2.4 |
| 7 | <10000 | 158 ± 16 | <10000 | 72 ± 2.6 |
| 8 | >10000 | 1330 ± 31 | >10000 | 277 ± 12 |

The invention claimed is:

1. A substituted benzamide derivative of Formula I:

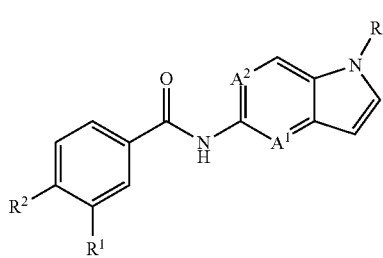

I $A^1$ is —N and $A^2$ is —CH; or $A^1$ is —CH and $A^2$ is —N; so that if $A^1$ is —N, then $A^2$ is —CH and if $A^2$ is —N, then $A^1$ is —CH;

R is a hydrogen atom, or represents branched or unbranched —($C_1$-$C_3$)-alkyl, —($C_1$-$C_3$)-alkyl, wherein one, two or three hydrogen atoms may be substituted by a halogen or hydroxyl, —($C_1$-$C_3$)—O—($C_1$-$C_3$), —($C_1$-$C_3$)—O—($C_1$-$C_3$), wherein one, two or three hydrogen atoms may be substituted by a halogen, or R is a group

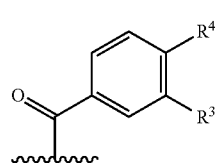

wherein $R^3$ and $R^4$ both together or independently are halogen, hydroxyl, —($C_1$-$C_3$)-alkyl, —($C_1$-$C_3$)-alkyl, wherein one, two or three hydrogen atoms may be substituted by a halogen or hydroxyl, —O—($C_1$-$C_3$)-alkyl, —O—($C_1$-$C_3$)-alkyl, wherein one, two or three hydrogen atoms may be substituted by a halogen, —O—($C_1$-$C_3$)—O—($C_1$-$C_3$), —O—($C_1$-$C_3$)—O—($C_1$-$C_3$), wherein one, two or three hydrogen atoms may be substituted by a halogen;

$R^1$ and $R^2$ both together or independently are halogen, hydroxyl, —($C_1$-$C_3$)-alkyl, —($C_1$-$C_3$)-alkyl, wherein one, two or three hydrogen atoms may be substituted by a halogen or hydroxyl, —O—($C_1$-$C_3$)-alkyl, —O—($C_1$-$C_3$)-alkyl, wherein one, two or three hydrogen atoms may be substituted by a halogen, —O—($C_1$-$C_3$)—O—($C_1$-$C_3$), —O—($C_1$-$C_3$)—O—($C_1$-$C_3$), wherein one, two or three hydrogen atoms may be substituted by a halogen, or a pharmaceutically acceptable salt thereof.

2. Substituted benzamide derivative of Formula I according to claim 1, wherein the benzamide derivative is a compound, selected from the group consisting of:
- 3,4-dichloro-N-(1H-pyrrolo[3,2-b]pyridin-5-yl)benzamide,
- 3-chloro-4-fluoro-N-(1H-pyrrolo[3,2-b]pyridin-5-yl)benzamide,
- 4-chloro-3-fluoro-N-(1H-pyrrolo[3,2-b]pyridin-5-yl)benzamide,
- 3,4-difluoro-N-(1H-pyrrolo[3,2-b]pyridin-5-yl)benzamide,
- 4-chloro-N-(1-(4-chloro-3-fluorobenzoyl)-1H-pyrrolo[3,2-b]pyridin-5-yl)-3-fluorobenzamide,
- 3,4-dichloro-N-(1H-pyrrolo[2,3-c]pyridin-5-yl)benzamide,
- 3-chloro-4-fluoro-N-(1H-pyrrolo[2,3-c]pyridin-5-yl)benzamide,
- 3,4-difluoro-N-(1H-pyrrolo[2,3-c]pyridin-5-yl)benzamide.

\* \* \* \* \*